(12) United States Patent
Womble et al.

(10) Patent No.: US 6,897,951 B2
(45) Date of Patent: May 24, 2005

(54) PROBE ASSEMBLIES FOR RAMAN SPECTROSCOPY

(75) Inventors: M. Edward Womble, Watertown, MA (US); Richard H. Clarke, Boston, MA (US)

(73) Assignee: Raman Systems, Inc., Austin, TX (US)

( * ) Notice: Subject to any disclaimer, the term of this patent is extended or adjusted under 35 U.S.C. 154(b) by 78 days.

(21) Appl. No.: 10/367,238

(22) Filed: Feb. 14, 2003

(65) Prior Publication Data

US 2004/0160601 A1 Aug. 19, 2004

(51) Int. Cl.[7] .............................. G01J 3/44; G01N 21/65
(52) U.S. Cl. ..................................................... 356/301
(58) Field of Search ......................................... 356/301

(56) References Cited

U.S. PATENT DOCUMENTS

| | | | |
|---|---|---|---|
| 5,112,127 A | | 5/1992 | Carrabba et al. |
| 5,139,334 A | | 8/1992 | Clarke |
| 5,377,004 A | * | 12/1994 | Owen et al. .................. 356/301 |
| 5,381,237 A | * | 1/1995 | Sela ............................ 356/301 |
| 5,534,997 A | | 7/1996 | Schrader |
| 5,657,404 A | | 8/1997 | Buchanan et al. |
| 5,862,273 A | | 1/1999 | Pelletier |
| 5,982,484 A | | 11/1999 | Clarke et al. |
| 6,018,389 A | | 1/2000 | Kyle et al. |
| 6,208,887 B1 | | 3/2001 | Clarke |
| 6,310,686 B1 | | 10/2001 | Jiang |
| 6,373,567 B1 | * | 4/2002 | Wise et al. .................. 356/301 |
| 6,621,574 B1 | * | 9/2003 | Forney et al. ............... 356/301 |

OTHER PUBLICATIONS

"RamanProbe" brochure published by InPhotonics (no publication date available).
Womble, M. Edward et al. "Low–Resolution Raman Method Offers Low Cost and Portability," Laser Focus World (Apr. 1999) pp. 131–136.

* cited by examiner

Primary Examiner—F. L. Evans
(74) Attorney, Agent, or Firm—Thomas J. Engellenner; Kevin M. Cronin; Nutter McClennen & Fish LLP

(57) ABSTRACT

Raman spectroscopy probe assemblies are disclosed for use with portable and/or handheld analyzers. The probes are also adaptable to sample liquids, and/or powders, tablets and/or other solids and are capable of withstanding harsh environmental conditions. The probes include an optical head assembly, associated optical fibers and replaceable sampling tubes. In one aspect of the invention, a simple orthogonal optical head assembly is disclosed that does not require collinear optical paths. The orthogonal arrangement of input and captured light paths also reduces the need for precise alignment of the optical components. The orthogonal optical head assemblies of the present invention are well suited to accommodate the shutoff mechanisms of the present invention. In another aspect of the invention, sampling tubes, and replaceable end caps for such tubes, are disclosed that facilitate hand measurements of substances.

19 Claims, 4 Drawing Sheets

PROBE ASSEMBLIES FOR RAMAN SPECTROSCOPY

BACKGROUND OF THE INVENTION

The technical field of this invention is Raman spectroscopy and, in particular, probes for analyzing samples in Raman spectroscopy systems.

It is known in the art that the chemical analysis of materials can be determined by optical spectrum analysis of samples. The optical analysis can be based on near or mid infrared (IR) spectroscopy. However, many liquids, especially aqueous solutions, do not exhibit simple IR spectrums. Moreover, mid IR spectroscopy is not well suited for fiber optic data transmission.

Raman spectroscopy provides an alternative approach to analyzing samples that is often better suited for aqueous and other liquid environments and, perhaps more generally, for applications where it is desirable to sample in-situ. Raman spectroscopy is an analytical technique that uses light scattering to identify and quantify molecules. When light of a single wavelength (monochromatic) interacts with a molecule, the light scattered by the molecule contains small amounts of light with wavelengths different from the incident light. The wavelengths present in the scattered light are characteristic of the structure of the molecule, and the intensity of this light is dependent on the concentration of these molecules. Thus, the identities and concentrations of various molecules in a substance can be determined by illuminating the substance with monochromatic light and then measuring the individual wavelengths and their intensities in the scattered light.

Until recently, the major drawback of Raman spectroscopy has been its expense relative to mid IR and near IR spectroscopy systems. A significant component of that expense is the monochromatic laser system required to produce quality, high-resolution spectra. Even using a laser diode as the scattering source, the laser remains as one of the major expenses in developing cost-effective Raman systems.

U.S. Pat. No. 5,139,334 issued to Clarke, and incorporated herein by reference, teaches a low resolution Raman spectral analysis system for determining properties related to the hydrocarbon content of fluids, in particular, the octane rating of gasoline. Different fuel properties are determined by a method that compares Raman-scattered light intensities over different wavelength ranges. Because the system uses low resolution analytical techniques, the constraints on the laser excitation source are significantly relaxed. This improvement, together with the continued miniaturization of electronic components has made lower cost, portable Raman spectrometers practical.

A variety of spectroscopic probes suitable for Raman spectroscopy are known in the art. Such probes are available, for example, from InPhotonics, Inc. of Norwood, Massachusetts. U.S. Pat. No. 5,112,127 is illustrative of such probe assemblies. Typically, the probe head is cylindrical with at least two fiber optic channels, one to carry excitation radiation to the sample and another to carry scattered Raman radiation back to a detector. The input and output light paths are arranged in a collinear fashion within the probe head and require precise alignment of various optical components within a small cylindrical space.

The size and shape of conventional probes typically preclude incorporation of any safety features, such as shut-off switches, into the probe head, itself. Moreover, in harsh process environments, conventional probes are also susceptible to damage by high temperatures, pressures and/or chemical solvents.

There exists a need for better Raman spectroscopic systems suitable for sampling liquids, tablets, powders and the like. Moreover, there exists a need for better probe designs for use with low-resolution Raman spectroscopic systems, especially with portable or handheld systems.

SUMMARY OF THE INVENTION

The present invention provides Raman spectroscopy probe assemblies that are easy to manufacture and are particularly suitable for use with portable or even handheld analyzers. The probes of the present invention are also adaptable to sample liquids, tablets and/or powders and are capable of withstanding harsh environmental conditions. The probes can include an optical head assembly, associated optical fibers for irradiating a sample and capturing Raman scattered radiation, as well as replaceable sampling tubes.

In one aspect of the invention, a safety shut-off mechanism is provided to reduce the risk of inadvertent exposure to radiation. In one embodiment, the shut-off switch is a spring-biased shutter that is opened by a solenoid only under predefined proper operating conditions.

In another aspect of the invention, a simple orthogonal optical head assembly is disclosed that does not require collinear optical paths. Instead, a orthogonal arrangement is disclosed that eliminates at least one turning mirror and the associated optical losses. The orthogonal arrangement of input and captured light paths also reduces the need for precise alignment of the optical components.

The orthogonal optical head assemblies of the present invention are well suited to accommodate the shutoff mechanisms of the present invention. The open architecture of the orthogonal assembly also facilitates the placement of lenses and/or filters within the head assembly, and also accommodates other elements, such as energy absorbing chambers or "beam dumps" within the head assembly.

In another aspect of the invention, sampling tubes are disclosed that facilitate hand measurements of substances, as well as liquid, tablet and/or powder sampling. The sampling tube preferably has an inner diameter that ensures that both the excitation light (and the Raman scattered light that is captured) are transmitted from (and back to) the optical assembly without substantial impingement on the inner surface of the tube. The sampling tube can be a detachable and/or replaceable element coupled to the optical head assembly, for example, via a threaded or other mechanical coupler. In one embodiment, the tube can include one or more lens elements that focus the excitation light at a location at or near the distal end of the tube. Alternatively, the lens can define a working zone in front of distal end, e.g., to sample a liquid volume or the like, or to sample through the wall of a container.

In yet another aspect of the invention, distal end caps are disclosed for the sampling tubes. In particular, for liquid or other hostile environments, the end caps can incorporate sealing elements, such as gaskets and an optical window that is impervious to the liquid. Suitable window materials include quartz and sapphire.

The end cap can also be used to position the probe at the proper distance for sampling. By matching the length of the cap (when attached to the sampling tube) to the focal power of the tube lens, the probe can be used for "point and click" contact measurements. The replaceable nature of the end caps also facilitates the use of calibration caps which need not transmit light but rather can position a calibration substance at or near the focus, which is irradiated to yield a scatter spectrum for comparison with a known standard (stored in the detector/data processor).

The method and apparatus of the present invention are broadly directed to using optical and mechanical components that carry light from a radiant energy source to a sample, and collect and redirect the light which has been scattered towards a radiant energy detector. In particular, the invention features using a tubular structure that allows multi-mode radiation to pass to the sample and scattered radiation from the sample for detection. The diameter of the tubular structure is selected to be wide enough to allows the radiation to pass without touching the walls of the tubular structure, thereby providing a signal that arises only from the sample. The tubular structure can also provide one or more lens elements that further serve to direct excitation light to the sample and/or collect light scattered from the sample.

The present invention is further directed to Raman spectroscopic systems that employ probes to determine the composition or properties of samples. Such systems, according to the present invention, can use a multi-mode laser in making a Raman spectroscopic measurement of the sample. The system can further include a light collector and/or a light dispersion element as well as a detector to measure spectral patterns indicative of the constituent or property of interest. The presence of an analyte and/or material properties can be determined by analyzing measured spectral data. In one preferred embodiment, the analysis is a low resolution analysis and compares Raman-scattered light intensities over different wavelength ranges.

In the low resolution Raman spectroscopy system, the probe transmits the scattered radiation captured by a sampling tube to a dispersion element. The dispersion element distributes the scattered radiation into different wavelength components. The detection array detects the scattered radiation in different wavelength ranges, and a processor processes the detected array data to detect the presence and/or quantity of a constituent of or to measure a property of the sample. The dispersion element can be a low resolution spectrometer. The low resolution spectrometer can be a monochromator. The detection array can be a diode array detector. Alternatively, the detection array can be a non-cooled charged coupled device detector.

The resolution of the system can be determined in part by the full width at half maximum (FWHM) of the spectral distribution of the multi-mode laser, and, in part, by the dispersion element. In one embodiment, the apparatus preferably has a resolution of between 10 cm$^{-1}$ and 100 cm$^{-1}$ and most preferably between 30 cm$^{-1}$ and 50 cm$^{-1}$. In one exemplary low resolution system, a multi-mode laser element is employed that produces laser radiation having a wavelength between about 700 nm and about 2.5 mm, more preferably between about 700 nm and about 1.1 mm. The multi-mode laser preferably has a power between about 50 mw and about 1000 mw. One example of a multi-mode laser element for use with the present invention is a 785 nm GaAs laser diode. This GaAs multi-mode laser has a spectral distribution FWHM of approximately 30 cm$^{-1}$.

The output can be analyzed through an integrated microprocessor system configured to provide output that identifies particular compositions. According to other features of the present invention, the processor can include a chemometric element for applying partial least square analysis to extract additional information from the Raman spectrum.

This invention is particularly useful in that it can provide a quick and reliable determination of material compositions and/or properties through a single spectral measurement on liquid samples. The present invention thus permits a chemical analysis to be determined without resort to an elaborate, multi-step analysis procedure requiring large quantities of sample. The use of optical fibers, multi-mode laser diodes, a low-resolution dispersion element and detector arrays allows the system to be small, portable, field-reliable, and sensitive to small amounts of constituents of interest. Furthermore, this configuration can provide an inexpensive device that would permit the continuous testing of the chemical components of a liquid, e.g., an organic liquid or biological sample.

The invention will next be described in connection with certain illustrated embodiments. However, it should be clear that various changes, additions and subtractions can be made without departing from the spirit or the scope of the invention.

BRIEF DESCRIPTION OF THE DRAWINGS

The invention will be more fully understood from the following detailed description taken in conjunction with the accompanying drawings, in which.

DETAILED DESCRIPTION

Figure 1:
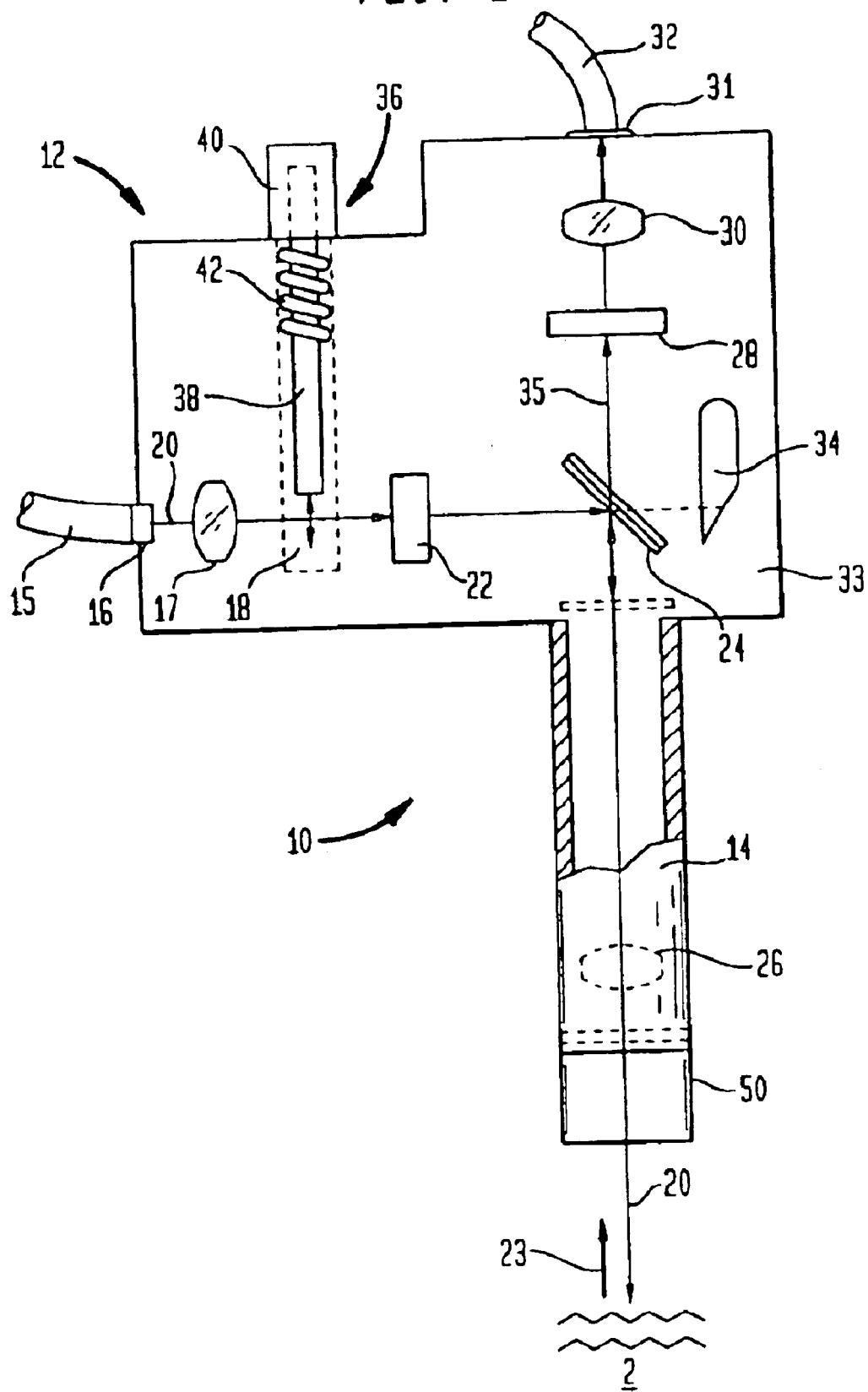
FIG. 1 is a partial cross-sectional schematic diagram of an optical head assembly and sampling tube for a probe according to the invention.

FIG. 1 is a schematic diagram of a probe 10 including an optical head assembly 12 and a sampling tube 14. Excitation radiation, e.g., from a portable or handheld Raman spectroscopy system, enters the head assembly 12 via input fiber 15. The input fiber can be coupled to the head assembly 12 via a coupler 16. The beam from the input fiber is passed through lens 17, which serves to collimate or other project the incoming radiation through the optical head assembly along beam path 20 with minimal dispersion. The radiation from the lens 17 then passes through chamber 18 of the safety switch 36. The incoming beam then passes through one or more optional filters 22, e.g., a low-pass filter.

The filtered incoming light is then reflected by dichroic beam-splitter 24 (which is designed to reflect nearly all of the excitation light) and directed into the sampling tube 14. Within sampling tube 14, a second lens 26 can be disposed to focus the excitation radiation to a particular point or region within the sample 2. For example, lens 26 can focus the light immediately in front of the end cap 50 for "point-and-click" operation of the probe.

The sampling tube 14 also serves to collect radiation scattered by sample 2 in response to the excitation beam 20.

The returning radiation 23 passes through lens 26 which now serves to collimate the scattered radiation and convey it to collection fiber 32. From the lens 26, the collected radiation travels along beam path 35, passing through dichroic beam-splitter 24 and, optionally, a mid-pass or long-pass filter 28 and lens 30. Lens 30 serves to focus the collected radiation into the output fiber 32 via output coupler 31. (It should be appreciated that the lens elements of the present invention can be simple or compound lens assemblies and that the functions that these optical elements perform—directing excitation radiation into a sample and collecting scattered radiation for analysis—can be achieved by various equivalent structures well known to those skilled in the art.)

The optical head assembly 12 can further include a "beam dump" 34 to capture and absorb incoming radiation that is not reflected by dichroic beam-splitter 24. The beam dump 34 can comprise a chamber that has been coated with suitable radiation absorbing material or otherwise formed or shaped to ensure that the radiation that is not directed into the sampling tube is captured and dissipated as heat.

The safety switch 36 is formed by a protective shutter, as shown in FIG. 1, that is disposed in a chamber 18 of the head block 33. The chamber 18 intersects the incoming beam path 20. Plunger 38 is disposed within chamber 18 and operatively connected to spring 42 and solenoid 40. In a an activated state, the solenoid 40, pulls the plunger 38 out of the light beam path 20, thereby allowing the multimode radiation to pass through the optical head assembly 12 and sampling tube 14 to the sample 2. In a deactivated state, ("laser blocking" position), the solenoid releases the plunger 38, which moves into the light beam path 20 and prevents the multimode radiation from passing through the probe 10. Thus, the switch 36 ensures that the probe remains in a "normally- off" state should a malfunction or power loss occur.

Figure 2:
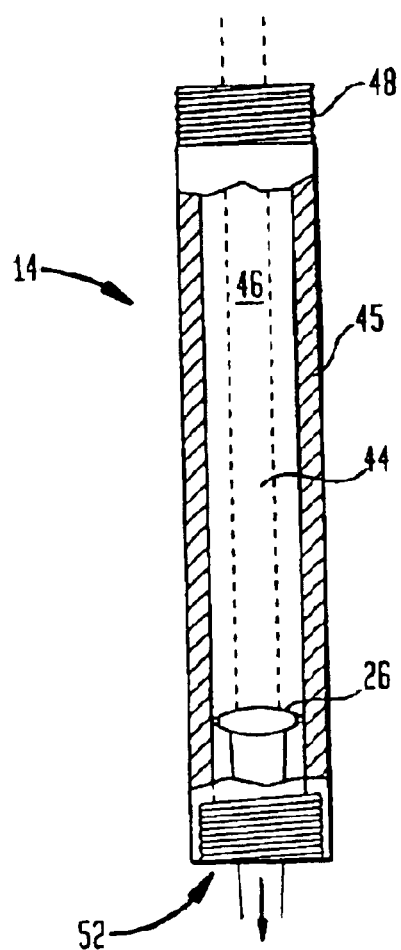
FIG. 2 is a partial cross-sectional schematic view of a sampling tube according to the invention.

In FIG. 2, a sampling to tube 14 according to the invention as shown in more detail. The tube 14 can include an externally threaded portion 48 that mates with an internal threaded recess in the aluminum block 33 of the optical head assembly 12, as shown in FIG. 1. Sampling tube 14 is hollow and includes a inner passageway 44 which is sufficiently wide so that both the incoming excitation beam and radiation collected from the sample (collectively, shown as the beam path 46) can propagate through the tube with minimal interaction with the tube walls 45. As noted above, lens 26 disposed in the sampling tube serves to both focus the excitation radiation and/or otherwise relay the collected radiation propagating through the tube. The sampling tube 14 can further include an internally threaded segment 52, adapted to receive a screw-on end cap.

Figure 3A:
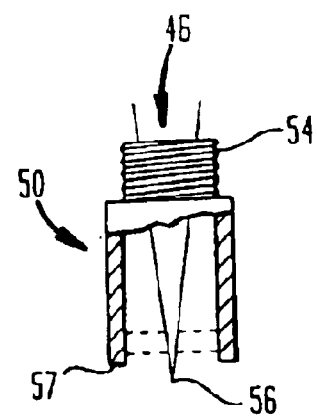
FIG. 3A is a partial cross-sectional, schematic view of an end cap for a sampling tube according to the invention.

FIG. 3A schematically illustrates an end cap 50 having an externally threaded portion 54 that couples to the internal threads 52 of the sampling tube. The end cap 50 can optionally include an distal window 56. In one preferred embodiment, the end cap is sized such that the radiation focused by lens 26 of sampling tube 14 converges to a point either in the same plane as the distal end of the end cap 57, or proximal thereto, for manual sampling.

Figure 3B:
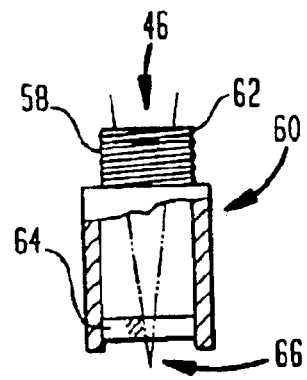
FIG. 3B is a partial cross-sectional, schematic view of an alternative end cap for a sampling tube according to the invention, particularly designed for fluid and/or powder sampling.

FIG. 3B is a schematic illustration of an alternative end cap 60 designed for use in harsh process environments, such as high temperature liquids, high pressure fluids and/or chemical solvent solutions. End cap 60 can include at least seal 62 (e.g., an O-ring or similar gasket) to ensure that the sampled fluid does not enter the sampling tube or the head assembly. End cap 60 of FIG. 3B can further include a protective window 64, preferably constructed of a fluid-impervious material, such as quartz, sapphire or the like.

Figure 3C:
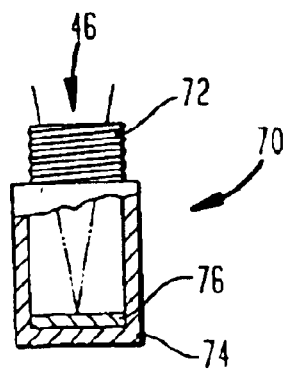
FIG. 3C is a partial cross-sectional, schematic view of an end cap for a sampling tube according to the invention, particularly designed for instrument calibration.

In FIG. 3C a calibrating end cap 70 is illustrated. This end cap similarly includes a threaded portion 72 adapted to couple with the sampling tube 14 but it is designed to not direct the beam 46 to a sample. Instead, the end cap 70 includes a calibration material 76 disposed or coated onto an inner surface of the end cap body 74 having a known Raman spectral signature. In use, radiation impinges upon the calibration material 76 and is reflected back through the sampling tube and the optical head assembly of the probe in order to calibrate the laser and/or analyzing components of the system.

Figure 4:
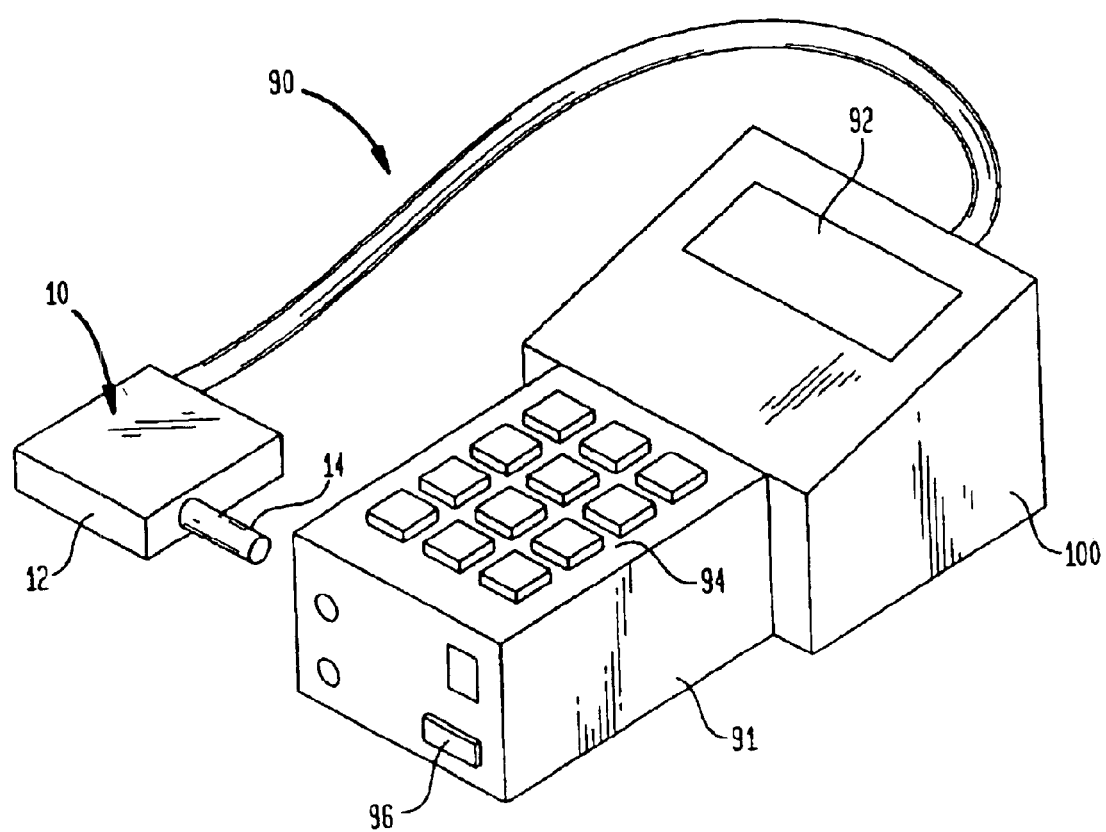
FIG. 4 is an overall schematic view of a portable Raman spectroscopy system employing a probe of the invention.

In FIG. 4 an overall Raman spectroscopy system 90 is shown including a probe 10 with its optical head assembly 12 and sampling tube 14 as well as a handheld analyzer/laser assembly 100. This system can include a handheld instrument 91 having a display 92, a keyboard or other user interface 94, and one or more communication ports 96 for receiving or downloading data from other sources.

Figure 5:
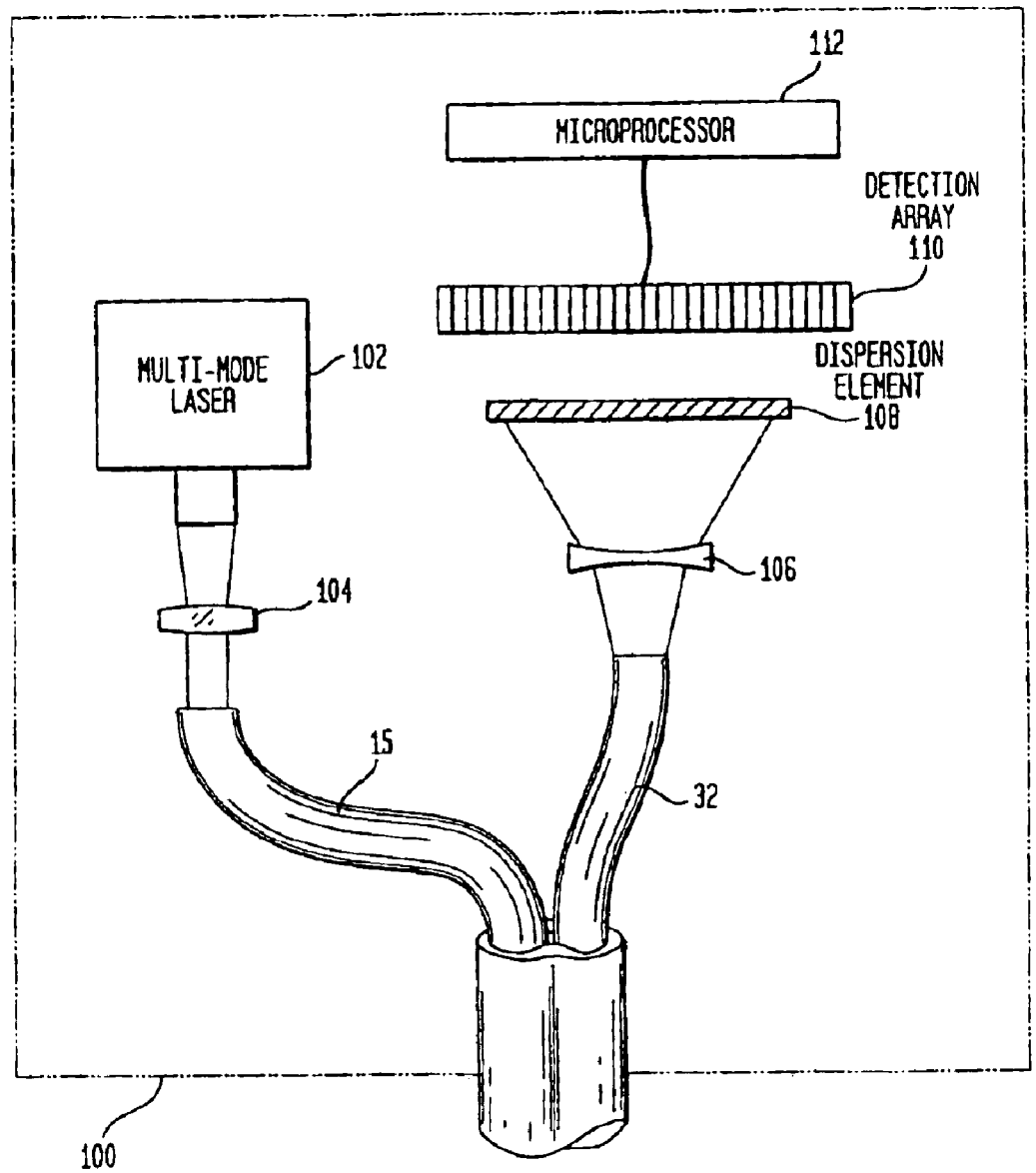
FIG. 5 is a block diagram of a laser/analyzer assembly for a Raman spectroscopy system according to the invention.

FIG. 5 is a schematic diagram of a laser/analyzer system 100 that is particularly well-suited for use with the probes of the present invention to perform sampling operations. System 100 includes a multi-mode laser source 102 and optional relay optics 104 connected to an excitation optical fiber 15 that carries the laser light to the probe. The The laser source 102 can be one of many multi-mode laser sources. For example, the B&W Tek multi-mode laser BWF-OEM-785-0.5, available from B&W Tek, Inc., of Newark, Del., can be used as the multi-mode laser. The Raman scattered light is collected by the probe and delivered via flexible optical fiber 32 to the analyzer assembly of system 100. The Raman scattered light travels through the fiber 32 (and optically via relay optics 106) into a low-resolution dispersion device 108 that serves to disperse the scattered light into its different wavelength components. The dispersed scattered light is detected by photodetector array 110 that, in this case, consists of a photodiode array or a charged-coupled device (CCD) array. The signals generated by the detector array 110 in response to the scattered light captured by the probe are then sent to a microprocessor 112 for analysis.

In the system 100, specific spectral bands of interest can be measured at low resolution to obtain the integrated band intensities. These bands can be narrow ones. The resolving power of the dispersion device 108 determines the position of specific wavelengths in the diode array in such a way that the signal from a particular diode in the array will typically correspond to the same (or a similar) narrow range of wavelengths. This combination of the low-resolution dispersion device 108 and the diode array photodetector 110 thus form a spectrometer. The microprocessor 112 selects a particular diode (or diodes) of the array 110 according to the property to be measured. The integrated signals lying in the two ranges can be arithmetically divided to form intensity ratios. The microprocessor 112 compares these ratios with known values or a correlating function to obtain an estimate of the chemical constituent or property of interest.

The terms "radiation" and "light" are herein utilized interchangeably. In particular, the term "light" can refer to radiation having wavelength components that lie in the visible range of the electromagnetic spectrum, or outside the visible range, e.g., the infrared or ultraviolet range of the electromagnetic spectrum. In certain embodiments of Raman spectroscopy, the preferred excitation wavelengths will range from about 700 nanometers to 2.5 micrometers. Although this portion of the electromagnetic spectrum is commonly known as infrared (IR) radiation, the term "light" will be used as shorthand expression in describing the path of this radiation as well as the various wavelengths of radiation induced by Raman scattering and collected for analysis.

Advances in the field of solid state lasers have introduced several important laser sources into Raman analysis. For high-resolution Raman systems the laser linewidth must be severely controlled, often adding to the cost of the excitation source and the system as a whole. For low resolution Raman spectroscopy (LRRS), however, the strategy of relinquishing resolution details in favor of emphasizing essential identifying spectral features, allows the use of a low cost, high energy multi-mode laser and a low resolution dispersion element. A multi-mode laser which can be used with a LRRS system, according to one embodiment of the present invention, is available in higher power ranges (between 50 mw and 1000 mw) than is available with a traditional single mode laser (<150 milliwatts). The higher power of a multi-mode laser increases the amount of scattered radiation available to the spectrometer system. The sensitivity of the LRRS system increases at least linearly with laser power.

A low resolution dispersion element can provide greater transmission of scattered radiation to the detector array. For example, a low resolution diffraction grating with wider slits than a typical diffraction grating can be used, providing greater transmission of incident scattered radiation to the detector array. Thus, the combination of a low cost, high energy multi-mode laser and a low loss dispersion element provides an inexpensive LRRS system that provides a high intensity signal.

In a typical LRRS application the need for feature separation is much like that encountered in mid-IR spectroscopy. The use of multi-mode lasers causes a degradation in the resolution of the spectrometer. The resolution of the LRRS system decreases primarily because the width of the laser line used to excite the sample is much larger with multi-mode lasers than it is with a single mode laser. A multi-mode laser has a linewidth of 2–3 nanometer. In comparison, a single mode laser has a linewidth of a fraction of a nanometer. However, one rarely requires single wavenumber resolution to find a spectral fingerprint feature that allows identification and quantification of a sample under analysis. Similarly, in LRRS, since the approach uses fundamental frequencies, even if not fully resolved, in the spectral analysis, a broader band laser source may suffice for the Raman analysis. In this case inexpensive, multi-mode solid state laser sources are both sufficient for the task and cost effective, and high power.

Since a Raman measurement is the difference in wavelength between the scattered light and the excitation line, an excitation line that has a larger spectral FWHM causes a proportional loss of resolution in the resulting Raman measurement. However, this reduction of resolution is offset by the advantages of lower cost and increased signal intensity. The increased signal intensity is a result of a higher energy laser source and wider slits in the diffraction grating allowing more light into the detector array. Since the spectrometer system resolution has been substantially reduced by the use of a multi-mode laser, the width of the slits can be increased with negligible effect on resolution. In addition, a CCD detector array can be matched to the lower resolution laser source and the dispersion element by reducing the number of elements in the array. For example, instead of 4096 array elements, one can use 2048 larger elements.

Thus, a complete LRRS spectroscopic system can consist of an inexpensive multi-mode laser diode operating at a higher power (between 50 mw and 1000 mw output) than traditional single-mode Raman sources and a low resolution monochromator matched to a simple CCD detector, with Rayleigh filtering provided by edge or notch filters capable of removing the excitation source background.

Various low resolution monochromators can be used as detector arrays. For example, Ocean Optics S-1000 and S-2000 monochromators are commercially available from Ocean Optics of Dunedin, Fla. Optical filters can be used to eliminate the Rayleigh line.

The optical fibers utilized in the probe apparatus of the invention can be multimode fibers, which are available from several commercial sources including, for example, Fiberguide, Inc. of Sterling, N.J. Their diameters may range from 1 $\mu$m to 1000 $\mu$m, preferably from about 100 $\mu$m to about 400 $\mu$m, and more preferably from about 100 $\mu$m to about 200 $\mu$m. Single fibers and fiber bundles can be utilized in the present invention.

The optic head assembly, sampling tubes and end caps of the probe apparatus can be constructed from various metallic materials, for example, aluminum, steel, copper or titanium. Preferred metals for this purpose include Hastalloy and stainless steel. The metallic material should be resistant to chemical deterioration and be able to withstand the adverse conditions to which the probe may be exposed to during use.

In constructing the sampling tube structures of the probe apparatus, the length can be selected based on the depth is to be inserted within the sample holder/chamber. For example, a longer length of tubular structure can be used where the fluid sample is enclosed within a deep container. A shorter tubular structure length can be used when the fluid in the sample is closer to the surface of the container. The range of lengths for the tubular structure can range from about 1 cm to about 25 cm, and more preferably from about 7 cm to about 15 cm.

The diameter of the tubular structure is selected such that it enables multi-mode radiation to pass through to the sample, and scattered radiation to pass from the sample without contacting the walls of the tubular structure. For example, the inner diameter of the tubular structure can range from about 3 mm to about 9 mm, and more preferably from about 5 mm to about 6 mm. The outer diameter of the tubular structure can range from about from about 10 mm to about 25 mm.

The end caps of the present invention are designed to allow the multimode radiation to pass through to the sample and the scattered radiation from the sample to be collected. The end caps can be constructed from the same materials as the sampling tubes. Suitable window materials for the end cap include, but are not limited to, glass, polycarbonates, other clear plastics, quartz and sapphire. In certain applications, the end cap material must also be resistant to corrosion or destruction in the liquid sample and, in such applications, quartz and sapphire may be preferred.

Probes can be constructed in accordance with the methods of he invention, with shapes and dimensions suitable for analyses of fluids, pills, tablets, powders and other materials, either directly or through the walls of transparent containers (e.g., bottles, bags and blister packs made from glass or plastics). Following construction, the sampling tubes of the probes can be either pressed against pills or tablets, powders and other solid objects or press against walls of their transparent containers. For liquids, the sampling tubes can be either inserted into the liquid or against the wall of a transparent container or conduit. The probes may be used to quantify or identify chemical compounds or their constituents.

The probes of the present invention can used for batch-by-batch analysis of a fluid sample, or for analysis of a continuous flow system, for example, to monitor a chemical reaction by Raman spectrometry. The probes can also be placed in a process stream of a manufacturing installation and connected to a Raman analytical instrument.

The probes use optical methods and apparatus for simplified remote measurement of the light transmitting or light scattering properties of a fluid, especially when it is necessary to confine the fluid to its natural process vessel, a pipe, or where environmental factors such as excessive temperature preclude the possibility placing light sources or detectors in the immediate vicinity of the fluid. The invention facilitates measurement of fluid properties over a broad range of applications, including but not limited to the determination of organic compositions of fluids, presence of analytes, and dissolved impurity levels in fluids.

Raman measurements can be made in a number of ways in the implementation of the present invention, for example, by comparing the characteristic Raman lines in a spectrum of a sample, with the number of characteristic lines with the standard spectra. Another example includes, comparing the ratio of intensities of two characteristic Raman lines which are common in the spectra for a particular constituent with the respective ratios with a standard of that constituent. The correlation of a previously stored spectrum may be used to determine whether the spectrum of the scattered Raman radiation is similar, and the resulting comparison may be displayed in a numerical form by the microprocessor.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A Raman spectrometer probe comprising:
   an input fiber through which radiation can propagate to irradiate a sample;
   a collection fiber through which radiation scattered by the sample can be coupled to a detector;
   an optical head assembly defining an input path and an output path, wherein the input path comprises at least one light directing element that receives excitation radiation from the input fiber and directs it to the sample and the output path further includes at least light collecting element that collects radiation scattered by the sample and couples the scattered radiation into the collection fiber;
   a sampling tube defining collinear input and output beam paths for transmitting light to a sample and collecting light scattered by the sample; and
   a removable end cap adapted to mate with the sampling tube and including a fluid impervious window.

2. The probe of claim 1, wherein the sampling tube further comprises at least one seal for sealing the end cap.

3. A Raman spectrometer probe comprising:
   an input fiber through which radiation can propagate to irradiate a sample;
   a collection fiber through which radiation scattered by the sample can be coupled to a detector;
   an optical head assembly defining an input path and an output path, wherein the input path comprises at least one light directing element that receives excitation radiation from the input fiber and directs it to the sample and the output path further includes at least light collecting element that collects radiation scattered by the sample and couples the scattered radiation into the collection fiber;
   a sampling tube defining collinear input and output beam paths for transmitting light to a sample and collecting light scattered by the sample; and
   a removable end cap adapted to mate with the sampling tube and including a calibration material.

4. The probe of claim 3, wherein the calibration material is positioned on an inner surface of the end cap body.

5. A Raman spectrometer probe comprising:
   an input fiber through which radiation can propagate to irradiate a sample;
   a collection fiber through which radiation scattered by the sample can be coupled to a detector;
   an optical head assembly defining an input path and an output path, wherein the input path comprises at least one light directing element that receives excitation radiation from the input fiber and directs it to the sample and the output path further includes at least light collecting element that collects radiation scattered by the sample and couples the scattered radiation into the collection fiber;
   a sampling tube defining collinear input and output beam paths for transmitting light to a sample and collecting light scattered by the sample, and including a sampling tube lens disposed therein for focusing the excitation radiation; and
   a removable end cap adapted to mate with the sampling tube, wherein the removable end cap is sized such that radiation is focused by the sampling tube lens in a region at the distal end of the removable end cap.

6. The probe of claim 5, wherein the removable end cap includes a distal window.

7. The probe of claim 6, wherein the cap is sized such that the radiation focused by the sampling tube lens converges to a point distal to the distal window.

8. A Raman spectrometer probe comprising:
   an input fiber through which radiation can propagate to irradiate a sample;
   a collection fiber through which radiation scattered by the sample can be coupled to a detector;
   an optical head assembly defining an input path and an output path, wherein the input path comprises at least one light directing element that receives excitation radiation from the input fiber and directs it to the sample and the output path further includes at least light collecting element that collects radiation scattered by the sample and couples the scattered radiation into the collection fiber;
   the input and output paths of the head assembly are substantially orthogonal and the head assembly further comprises a dichroic mirror that directs the excitation radiation to the sample by reflection and transmits scattered radiation returning from the sample to the output path; and
   the optical head assembly further comprising a beam energy dump for absorbing radiation from the input path that is not reflected by the dichroic mirror.

9. The probe of claim 8, wherein the optical head assembly further comprises a shutter, positioned along the input path prior to the beam energy dump, for blocking the input path when the probe is not in use.

10. The probe of claim 9, wherein the shutter is spring-biased in a closed position.

11. The probe of claim 8, wherein the light directing element comprises a collimating lens disposed in the input path.

12. The probe of claim 8, wherein the optical head assembly further comprises an input optical filter disposed in the input path.

13. The probe of claim 12, where the input optical filter is a short-pass filter.

14. The probe of claim 8, wherein the probe further comprises a sampling tube defining collinear input and output beam paths for transmitting light to a sample and collecting light scattered by the sample.

15. The probe of claim 14, where the sampling tube further comprises at least one lens element for transmitting light to a sample and collecting light scattered by the sample.

16. The probe of claim 8, wherein the optical head assembly further comprises an output optical filter disposed in the output path.

17. The probe of claim 16, where the output optical filter is a long-pass filter.

18. The probe of claim 8, wherein the light collecting element comprises a focusing lens for focusing collect light into the output fiber.

19. The probe of claim 14, wherein the sampling tube further includes a removable end cap.

* * * * *